(12) United States Patent
 Michaut

(10) Patent No.: US 9,052,273 B2
(45) Date of Patent: Jun. 9, 2015

(54) METHOD AND INSTALLATION FOR ULTRASOUND INSPECTION OF BUTT-WELDING OF TWO TRANSVERSE ENDS OF TWO METAL STRIPS

(75) Inventor: Marc Michaut, L'Horme (FR)

(73) Assignee: Primetals Technologies France SAS, Savigneux (FR)

( * ) Notice: Subject to any disclaimer, the term of this patent is extended or adjusted under 35 U.S.C. 154(b) by 288 days.

(21) Appl. No.: 13/642,988

(22) PCT Filed: Aug. 12, 2010

(86) PCT No.: PCT/EP2010/061783
§ 371 (c)(1),
(2), (4) Date: Oct. 23, 2012

(87) PCT Pub. No.: WO2011/131252
PCT Pub. Date: Oct. 27, 2011

(65) Prior Publication Data
US 2013/0036820 A1     Feb. 14, 2013

(30) Foreign Application Priority Data

Apr. 23, 2010    (EP) .................................. 10290219

(51) Int. Cl.
*G01N 29/04*     (2006.01)
*G01N 29/24*     (2006.01)
*B23K 31/12*     (2006.01)

(52) U.S. Cl.
CPC .......... *G01N 29/2418* (2013.01); *B23K 31/125* (2013.01); *G01N 29/041* (2013.01); *G01N 2291/0423* (2013.01); *G01N 2291/2675* (2013.01)

(58) Field of Classification Search
CPC ....................................................... G01N 29/04
USPC ........... 73/601, 597, 598, 600, 602, 618, 622, 73/624, 625, 627
See application file for complete search history.

(56) References Cited

U.S. PATENT DOCUMENTS 5,153,677 A * 10/1992 Keck et al. ..................... 356/482
5,190,204 A     3/1993  Jäck et al.
(Continued)

FOREIGN PATENT DOCUMENTS

EP        0845309 A1      6/1998
EP        2039458 A1      3/2009
(Continued)

OTHER PUBLICATIONS

Mi Bao et al: "Three-dimensional ray tracing of laser ultrasound for weld penetration sensing", The Journal of the Acoustical Society of America, American Institute of Physics for the Acoustical Society of America, New York, NY, US, vol. 115, No. 4, Apr. 1, 2004, pp. 1565-1571, XP012072214, ISSN: 0001-4966, DOI: DOI:10.1121/1.1649942.

(Continued)

*Primary Examiner* — J M Saint Surin
(74) *Attorney, Agent, or Firm* — Laurence A. Greenberg; Werner H. Stemer; Ralph E. Locher

(57) ABSTRACT

A method and installation for inspecting a butt weld of transverse ends of metal strips held together between first and second jaws along the ends, include leaving an interstice between the jaws for passage of a first transmission channel of incident waves generating ultrasound waves on one surface of the first strip and enabling passage of a second transmission channel of waves emerging from the surface of the second strip. The incident waves of the first channel are generated using laser pulses in an operating state implementing a third channel of waves generated on the surface of the first strip, passing through the weld, and emerging in the second channel. Weld inspection characteristics are identified by analyzing the operating state related to the pulses and a measurement of a signature of a vibration state of the surface of the second strip upon emergence of the waves in the second channel.

17 Claims, 1 Drawing Sheet

(56) References Cited

U.S. PATENT DOCUMENTS

| | | | |
|---|---|---|---|
| 5,948,295 A | 9/1999 | Perret et al. | |
| 6,747,268 B1* | 6/2004 | Ume | 250/227.11 |
| 6,802,929 B2* | 10/2004 | Ruotsalainen | 156/272.8 |
| 7,168,322 B2* | 1/2007 | Bardoux et al. | 73/588 |
| 7,492,449 B2* | 2/2009 | Ume et al. | 356/237.1 |
| 7,762,136 B2* | 7/2010 | Ume et al. | 73/597 |
| 8,243,280 B2* | 8/2012 | Dubois et al. | 356/502 |
| 8,387,462 B2* | 3/2013 | Yamano et al. | 73/632 |
| 2008/0072674 A1 | 3/2008 | Ume et al. | |

FOREIGN PATENT DOCUMENTS

| | | |
|---|---|---|
| JP | S63180853 A | 7/1988 |
| JP | H04220183 A | 8/1992 |
| JP | H08136512 A | 5/1996 |
| JP | H11271281 A | 10/1999 |
| JP | 2001318081 | 11/2001 |
| JP | 2008545123 A | 12/2008 |
| RU | 2057331 C1 | 3/1996 |
| SU | 590659 A1 | 1/1978 |
| SU | 1350608 A1 | 11/1987 |
| WO | 2009037351 A1 | 3/2009 |

OTHER PUBLICATIONS

Kopylow C. et al.: "Laser Ultrasound—A flexible tool for the inspection of complex CFK-components and welded seams", Proceedings of SPIE, PO Box 10 Bellingham WA 98227-0010 USA, vol. 6616, 2007, pp. 66163J-1-66163J-12, XP040242519.

* cited by examiner

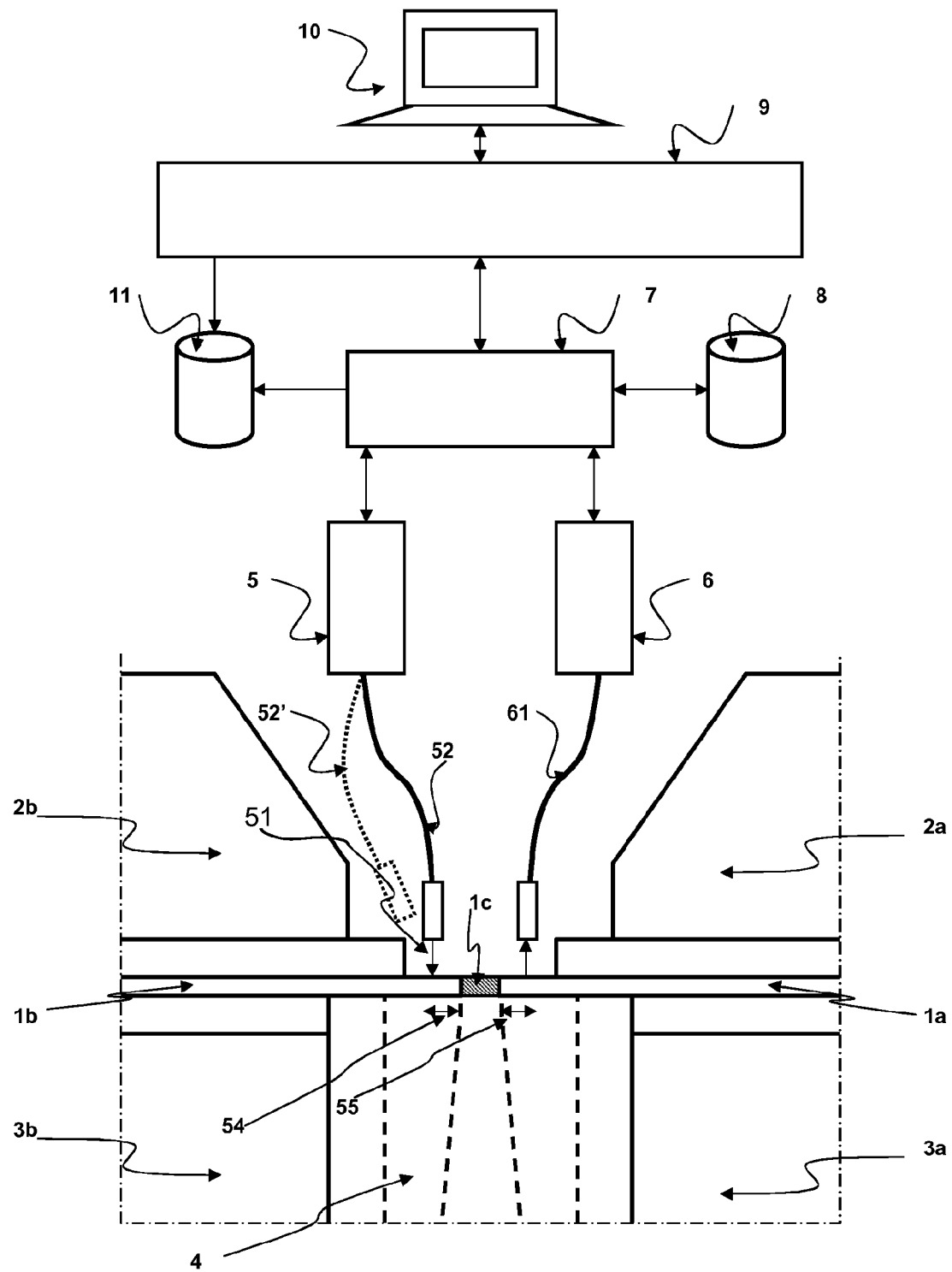

METHOD AND INSTALLATION FOR ULTRASOUND INSPECTION OF BUTT-WELDING OF TWO TRANSVERSE ENDS OF TWO METAL STRIPS

BACKGROUND OF THE INVENTION

Field of the Invention

The present invention relates to a method for inspecting butt welds between two transverse ends of two metal strips, in which the ends are brought together and held between a first jaw and a second jaw disposed along each of the transverse ends. The present invention also relates to a nondestructive weld-testing installation used for this purpose.

The invention relates to the butt welding of metal strips, in particular steel, running through a processing installation for rolling, pickling, coating, etc., hereinafter referred to generically as a "processing installation". It relates specifically to the non-destructive testing of butt welds.

With a view to improving the productivity of cold-rolling and processing installations for steel strips by avoiding the coil-by-coil processing thereof, modern high-capacity installations operate continuously by welding successive strips to one another, connecting the tail of a newly processed strip to the head of a new strip.

During this butt welding operation, the movement of the two approximated strip ends to be welded is stopped and the downstream sections of the processing installation are fed by a strip-accumulation device pre-loaded between two successive welds.

This technique is well known to the person skilled in the art, and it helps to speed up the butt-welding operation in order to limit the time the strip ends are stopped and, consequently, the capacity and cost of the accumulation devices. It also addresses the need to create strong, sound welds that are not liable to break in the processing installation or to damage certain parts thereof as it runs through the different machines therein.

The butt welding operation is performed by a welder comprising, in addition to the welding device itself (flash, resistance-seam, TIG, MIG, laser, laser-hybrid butt welding), two clamping jaws, each one being designed to immobilize one of the strips or sheets coiled (or at least uncoilable), one located downstream in the direction of movement of the strip and intended to immobilize the tail of the coil engaged on the line, the other located upstream and intended to immobilize the head of the recently inserted coil.

This type of welder must be able to produce high-quality welds first time. Indeed, the breaking of a weld during movement of the strip through the installation or the need to redo an incorrect weld can generate significant production losses. The quality of a weld depends on multiple, inseparable key factors based essentially on the following criteria:

The metallurgical quality of the welded joint, in particular for steels liable to metallurgical alterations of the heat-affected area, The welded section, which should ideally be free of over-thickness and under-thickness, The continuity and compactness of the welded joint.

Metallurgical quality depends on the method used and the heat cycle it causes in the affected area, as well as different pre- and post-heating treatments or annealing treatments performed locally in the welder itself or immediately downstream thereof.

The welded section depends on the method and the finishing means implemented following welding. Flash butt welding produces a bead that needs to be planed and flash butt welders are usually fitted with an integrated planing unit. Resistance seam welding also generates an over-thickness due to the overlapping of the sheets to be welded, which usually needs to be crushed using roller devices built into the welders. Laser welding enables precise management of the welded section associated with a very limited heat-affected area.

The continuity and compactness of the joint depend essentially on the welding parameters used. These parameters are mainly electrical and are usually easy to manage reliably.

However, the straightness of the edges to be welded and the relative positioning thereof during welding are also essential parameters as they relate to the continuity and compactness of the joint as well as the cross-section thereof.

In order to guarantee the quality of the butt weld, the strip ends to be welded must be perfectly aligned and straight. To ensure this, welders usually include two clamping jaws intended to immobilize the sheets, one of which is located downstream in the direction of movement of the strip and is intended to immobilize the tail of the strip belonging to the coil on the line, while the other is located upstream and is intended to immobilize the head of the strip belonging to the coil that has just been introduced in order to connect it to the preceding strip. The strip ends are therefore immobilized in the clamping jaws, projecting beyond them by an overhang generated by their precise and clean shearing effected using shears built into the welder or a laser beam. This overhang must be as small as possible along the neighboring ends to be welded in order to keep them correctly aligned and to control any play or lack of play.

Despite all of the measures taken to ensure that all of the geometric, metallurgical and welding-parameter conditions are satisfied, some welds still have defects that may cause a breakage during movement through the processing installation. Such incidents may have serious consequences, in particular if the breakage occurs in a continuous-annealing or galvanizing furnace. The installation may then be stopped for several days to re-establish strip continuity.

Other defects or imperfections have much less serious consequences, such as excessive over-thickness, which would for example require the rollers of a skin-pass mill to be opened and the loss of several meters of strip not skin-passed upstream and downstream of the weld. Multiple incidents of this type can then significantly reduce the casting yield of the coils processed in the processing installation. It is therefore particularly important that the operator be confident that the weld is of sufficient quality before it leaves the welding machine for the installation.

To ensure this, a visual examination of the weld is performed at most installations, sometimes using a camera. This decision-making process depends on the vigilance and experience of the operator, and is usually conservative, resulting in re-welds that are not necessarily required.

In some cases, thermometry and infrared cameras are used. This is a significant advance, particularly since the most sophisticated installations have image-processing systems. Nonetheless, these devices are generally placed above the upper face of the strip and the weld to be checked, the lower face being barely accessible in a welding machine.

In other cases, the electrical and movement parameters are simply checked against the programmed parameters to guarantee a correct weld.

To date, only these means are used to inspect these types of weld and there are no means for detecting the presence or harmfulness of internal defects, in particular those related to the internal structure of the "strip-weld-strip" complex, i.e.

the molten area of the edges to be welded (and any added metal) that joins said edges to be welded and the adjacent unmolten "heat affected" areas, where different metallurgical transformations occur, along with very subtle emerging defects such as cracks or un-welded areas the primary plane of which is substantially parallel to the light rays captured by the operator or the cameras used.

Furthermore, as mentioned above, the spacing used to minimize the overhang of the ends held in the jaws must be limited, and this prevents the weld from being seen correctly and hinders thermometric/electric measurement. Finally, also in consideration of these facts, if the weld is not checked while the ends are still held in the jaws, and if the inspection has to take place after the jaws have been released from the strip clamping position, and if a defect is detected according to the prior art, the strip will inevitably need to be reinserted and repositioned in the welder in order to re-cut it and restart the welding operation, with all of the drawbacks that this entails.

BRIEF SUMMARY OF THE INVENTION

An object of the present invention is to propose a method for inspecting a butt weld of two transverse ends of two metal strips before they are released from the tight grip of the clamping jaws used during welding, said method enabling in particular an inspection of external and internal defects related to the "strip-weld-strip" structure. In order to implement this method, another object of the invention is to provide a suitable installation.

An inspection method and an installation enabling the implementation thereof are therefore presented below.

The invention therefore proposes a method for inspecting a butt weld of two transverse ends of two metal strips, said ends being brought together and held between a first jaw and a second jaw along each of the transverse ends, characterized in that:

at least one space is left between the first jaw and the second jaw such that an interstice is formed in order to permit the passage of a first transmission channel of incident waves able to generate ultrasound waves on one surface of the first strip and to enable the passage of a second transmission channel of waves emerging from the surface of the second strip;

the incident waves of the first channel are generated using laser pulses in an operating state at least designed to implement a third channel of ultrasound waves generated on the surface of the first strip, passing through the weld, and emerging in the second channel;

weld inspection characteristics are extracted for identification by means of a step (7) for analyzing the operating state related to the pulses and at least one cleanliness measurement, such as a vibration-state signature of the surface of the second strip upon emergence of the ultrasound waves in the second channel.

In other words, the method according to the invention can be used to non-destructively test the butt welds of two ends of coils of steel strip in a rolling or processing installation in which the end of one strip uncoiled in said installation is stopped between the "output" jaws of a welding machine while the head of a new strip is brought between the "input" jaws of the same welding machine, the two strip ends so clamped in the jaws being cut to make the geometric features thereof suitable for welding, moved by moving the jaws into a welding position then welded together using a suitable method, such as laser beam, plasma-arc, arc, resistance-seam or flash-butt welding.

The method according to the invention is characterized in that it must be possible to position the devices used to send (or generate) and to receive the ultrasound waves in the very small space between the jaws of the welding machine, i.e. in the case of a laser welding machine, a space that may be less than 10 mm in the direction transversal to the weld. They must also enable very quick movement without coupling issues with the strip and withstand an environment that may be hot if, for example, said devices for maintaining the first and second channels are immediately adjacent to a laser welding head.

In this small space between the jaws of the welding machine, the method according to the invention can guarantee that:

The ultrasound waves are generated at the output of the first channel onto a surface of the strip, said output moving contactlessly above one of the two strip ends, in parallel to the weld, and along the entire length thereof.

The ultrasound waves so generated pass through the butt weld and are captured by a receiver via the second channel having an (optical) wave collection input moving contactlessly above the other end of the strip, in parallel to the weld and along the entire length thereof, along a path parallel and synchronous to the path of the transmitter.

The ultrasound waves captured by the receiver are analyzed by an analysis device able to identify at least one characteristic datum of the wave transfer between the transmitter and the receiver, such as attenuation, travelling time or wave transformation.

The characteristics of the wave transfer are compared to a library of transfer anomalies related to different types of welding defects.

The analysis system quantifies the severity of the defect on the basis of the type of defect identified and the extent thereof along the length of the weld.

In particular, the first and second channels have a small-section optical guide sufficient to enable an incidence at a point or emergence which can be detected at a point on the edge of the weld and on one side of each strip. Experience shows that at least one optical fiber or wave collimator having a cross-section of less than approximately 10 mm may be used to form said wave transport channels in an optical spectral domain. Accordingly, the overhang cited in the introduction to the invention can be very small knowing that the space providing an adequate interstice between the jaws remains in practice identical to the one usually required for the correct maintenance of the ends outside the scope of the invention. Inspection is therefore possible without having to separate the jaws or, in other words, without releasing the strip ends from the jaws.

Using the ultrasound and optical waveguide in the form of the three channels mentioned above, the incident optical waves coming from the first channel generate ultrasound waves which propagate in the third channel, i.e. in a part of the first strip, through the weld and finally in a part of the second strip before finally being able to emerge in the second channel (in the form of ultrasound waves then optically detectable surface vibrations), said second channel being provided to engage the stage in which the waves emerging from the second strip are analyzed.

The physical properties of these ultrasound waves are modified through propagation thereof both on the surface of the strip-weld-strip structure and in the volume of said structure, thereby materializing said third channel. Thus, they carry at least one inspection characteristic of the weld which can then be identified using predefined criteria, for example by prior classification of the types of wave modifications analyzed in an ideal weld or a weld having one or more defects typically recognizable by a catalogued signature of a wave signal outputted from the second channel. The physical generation principle of said ultrasound waves is also known by the technical name "laser ultrasonics", but the invention does not further develop this theory. Instead, the invention focuses on an inspection method in welding position, which makes it possible to use this physical principle as part of a sequence of innovative steps required by a welding cycle, enabling an efficient and instantaneous final analysis of the complex strip-weld-strip structure, ideally by means of a signature analysis measured using a vibration state of the ultrasound waves implying a welding defect, said measured signature being comparable and identifiable with the signatures of typical defects catalogued in a database. Analysis by comparison of measured/catalogued signatures is therefore simple and rapid, since it does not require complex knowledge or, at least, having to implement algorithms to extract complex physical properties of the propagation behavior of ultrasound waves in a strip-weld-strip structure that is also extremely complex for different defect types.

The inspection characteristics of the weld may also for example be deduced by measuring attenuation, traveling time or wave transformation by measuring the waves via the second channel. Depending on the characteristics or, at least, the signatures derived from inspection of the weld, alarms are generated in order to immediately flag a potential defect.

The method according to the invention provides for pulses to be sent by a laser transmitter coupled to the input of the first channel and the waves of the second channel are captured by a receiver coupled to the output of the second channel;

an output of the first channel and an input of the second channel are slid along the space above or through the interstice between the two jaws without touching the strip, such as to extract the inspection characteristics or signatures of the weld in two ways:

synchronously and during a time period as short as possible in relation to the welding device itself carried by a mechanism slid along the space between the two jaws.

after completion of the welding of the ends of each strip.

The sliding of the output of the first channel and of the input of the second channel therefore enable an inspection during the welding and after the welding along the strip ends without needing to move the "strip-weld-strip" structure in relation to the sliding movement.

Depending on the welding method used, the contactless movement of the output of the first channel and of the input of the second channel above the two strip ends in the interstice provided, in parallel to the weld, and along the entire length thereof may be performed:

at the same time as the weld and at the same speed in the case of progressive welding methods, such as resistance-seam, TIG, MIG, laser or laser-hybrid welding. In this case, the output of the first channel and the input of the second channel are arranged behind the welding head, on the same movement device as the welding head or on a movement device separate therefrom that is nonetheless synchronous with the moving device of said welding head.

after completion of the weld for flash-butt welding.

The method can also be implemented using one of the following modes:

A learning mode systematically involving an expert to confirm or modify the identification and quantification of a welding defect (recognition of typical signature of a defect);

An automatic mode in which the analysis step related to the inspection characteristics of the weld independently identifies and quantifies at least one welding defect (by adequate recognition of a signature of said defect) and issues subject to a predefined tolerance at least one alarm to an operator;

A semi-automatic mode in which, as part of the preceding automatic mode, if the ultrasound wave transfer characteristics/signatures are liable to be inadequately identifiable, an additional-inspection decision request is sent to an operator.

Additionally, the method according to the invention can be implemented using at least one of one of the following modes:

A learning mode systematically involving an expert who, on the basis of the identification and quantification of a welding defect, corrects the appropriate welding parameters, such as the movement speed of a welding head or the welding power in order to correct said defect;

An automatic mode in which the analysis step related to the weld-inspection characteristics/signatures independently corrects the welding parameters based on identification and quantification of a welding defect;

A semi-automatic mode in which, as part of the preceding automatic mode, the analysis step issues a welding-parameter correction request to an operator on the basis of identification and quantification of the welding defect.

These implementations of the method according to the invention therefore provide a high degree of flexibility in inspections, clarifying all doubts concerning welding defects rapidly, i.e. flexibly during and/or after welding, and in particular before the strip leaves the welding position for other process stages where a welding defect would be prejudicial.

The method according to the invention provides, in particular with a view to analysis steps after an inspection step, for any faults identified and quantified to be recorded in a database, in the form of signatures catalogued jointly and for each defective weld, with the welding parameters used and data concerning the strips welded. Accordingly, the analysis step enables inspection accuracy to be increased in consideration of complex and changing strip-welding settings and situations, with a view to obtaining as much data as possible to enable the subsequent analysis of the defects identified and quantified. Off-line analyses may also be carried out in order to study defect occurrence conditions statistically and improve welding parameters.

The method according to the invention also enables ultrasound waves on the surface of the first strip (coming from the first channel) to be generated by a pulse laser (coupled to the input of the first channel) under at least one of the two operating states below:

a thermoelastic operating state;

a thermoelastic operating state alternating with an ablation operating state, said alternation being in particular determined by the analysis step, in the event of an anomaly or doubt concerning an alert, with the possibility of carrying out an additional analysis of the characteristics related to a wave transfer. With two alternating operating states, it is advantageously possible to obtain two alternating vibration state signatures of the ultrasound waves passing through the strip-weld-strip structure, which makes the inspection more reliable, in particular if there is any doubt concerning one of the two signatures measured. Accordingly, superfluous alerts can be avoided and the welding inspection is therefore more robust against measurement artifacts.

Indeed, in order to fit in the very small space between the jaws of the welding machine and to enable quick movement without coupling problems with the strip, the ultrasound-wave transmission device is a pulsed laser generating an ultrasound vibration on the surface of the strip in a "thermoelastic" operating state, i.e. without fusion. This thermoelastic operating state is favorable for generating Lamb or surface waves, i.e. waves that propagate substantially parallel to the surface of the strip.

Alternatively, the ultrasound waves are generated alternately in thermoelastic and "ablation" operating states. The ablation operating state involves very localized fusion on impact of the beam and encourages the generation of longitudinal bulk waves, i.e. waves that propagate substantially perpendicular to the surface of the strip.

The different nature of the ultrasound waves generated by the laser transmitter leads to very different wave transfer characteristics for a single weld. For certain types of wave-transfer anomaly identified, the analysis device may require the modification of the laser shot parameters (power and duration) in order to fit ablation pulses in between thermoelastic pulses. The double "signature" of the welding defect improves diagnostic reliability. Such a method may also be required by the analysis device if the characteristics of the wave transfer in a thermoelastic operating state are undocumented or barely documented in the signature library or database.

In order to improve the detection of minor defects by improving the signal-noise ratio outputted from the second channel, the method according to the invention provides for an ultrasound signal captured by the second channel to undergo a synthetic aperture focusing technique (SAFT) process before the analysis step.

In order to implement the method according to the invention, an installation for the non-destructive testing of the welds of two strip ends held in the aforementioned jaws is characterized particularly in that at least one of the two first or second ultrasound wave channels includes at least one optical guide (optical fiber(s), collimator and/or focalizer) that move contactlessly above the surface of the strip ends, in parallel with a welding path. This optical guide (ideally one or more optical fibers) has a limited footprint and enables incident and emergent channeling of ultrasound waves through a very small cross-section between the two jaws and on either side of the weld, respectively on one side of each end of the approximated strips.

The welded zone can therefore be scanned as the welding is performed, which helps to optimize the cycle time, for example by moving behind a laser welding head. It may also be scanned after welding, for example in the case of flash welding.

The second channel is coupled to a receiver sensitive to the vibrations of the surface of the strip generated by the ultrasound waves, such as an interferometer, and the second channel includes at least one optical guide having a wave collecting end that moves contactlessly in the interstice between the jaws, along a path parallel and synchronous to the path of the ultrasound waves on the side of the first strip.

The output of the first channel and the input of the second channel are moved contactlessly above the strip ends and can be synchronized with or delayed in relation to a welding operation along one predefined length of the ends.

The pulses are ideally generated by a pulsed YAG laser at the input of the first channel, and they are guided by the first channel and generate the ultrasound waves at the output of the first channel by incidence on the surface of the first strip.

The output of the second channel is coupled to an ultrasound wave receiver or at least a receiver optically sensitive to the vibrations of the surface of the strip caused by the ultrasound waves. The receiver is preferably a confocal Fabry-Perot or photo-induced electromotive force (PI-EMF) interferometer that can be coupled to a continuous or pulsed laser generating a plane of reference.

The axis of the transmitting end of the optical fiber path of the laser transmitter and the axis of the receiving end of the optical fiber path of the interferometric receiver are substantially perpendicular to the surface of the strip or may be slightly inclined towards the weld.

A set of sub-claims also sets out the advantages of the invention.

BRIEF DESCRIPTION OF THE SEVERAL VIEWS OF THE DRAWING

An exemplary embodiment and application is provided using the FIGURE described:

The single FIGURE of the drawing is a diagram of an installation enabling implementation of the method according to the invention in a strip welding machine (shown in cross section).

DESCRIPTION OF THE INVENTION

A tail of a first strip (1b) is clamped in the output jaws (2b, 3b) of a welding machine. The head of a second strip (1a) is clamped in the input jaws (2a, 3a) of said welding machine.

The input and output jaws are in an approximated welding position and the two strip ends (1a, 1b) are joined by a weld (1c) to be inspected. A supporting element (4) may provide additional support for the strip ends.

A transmitter (5), for example a pulsed YAG laser, transmits a laser beam (51) along an optical-fiber path (52), this being the first channel described in the method according to the invention. The impact of the laser beam on the first strip generates, for example in thermoelastic mode, i.e. without fusion of the strip, ultrasound waves on the surface (in this case the upper surface) of the first strip (1b) that propagate towards/into the weld (1c) and then the second strip (1a). These waves cause mechanical movements normal to the surface of the strip that can be detected by an interferometric device (6) by means of a fiber-optic path (61), this being the second channel for waves optically influenced by the vibration state of the surface of the strip caused by the ultrasound waves. Optionally, a first channel is shown using dotted lines in a position (52') enabling an inclined incidence of one of the fiber-optic paths in relation to the strip facing it. The third wave channel is materialized by the "strip-weld-strip" join (54, 1c, 55) on and in which the waves are propagated. It is essential that at least one space is left between the first and second jaws such that an interstice (54, 55) is formed to enable the passage of the first optically incident channel (52) to generate the ultrasound waves on the surface of the first strip (1b) and to enable the passage of an optically emergent second channel (61) to capture the waves emerging from a surface of the second strip (1a). The width of the interstice (54, 55) about the weld, being at least the distance permitted between the axes of the first and second channels, is made as small as possible on account of the approximation required by the jaws and may, if required, be variably adapted within a maximum width permitted by the jaws, in order to better extract the target welding characteristics that require precise incidence points at a given distance from the weld. Several signatures may also advantageously be measured depending on the configurations within the variable distances between the first and second channels.

An analysis device (7) (used to perform the analysis step according to the invention) receives the signals generated by the interferometer (6) via the second channel and the data coming from a PLC system (9) controlling the welding machine. These data relate, for example, to the thickness of the strip, the grade of the steel and all of the welding parameters, as well as the settings of any devices used to apply heat treatments before or after the weld. It identifies at least one datum characteristic of the wave transfer, or signature, between the transmitter (5) and the receiver (6), such as attenuation, traveling time, wave transformation or any other targeted/recognizable anomaly characteristic of the strip-weld-strip structure, and it searches a data library (8) for a potential match between these wave-transfer anomalies and a type of welding defect, ideally by recognition of a single signature or a double signature. It quantifies the severity of the defect and, using the PLC system (9), is able to generate an alarm on the operator control console (10) if the defect requires the weld to be redone. It can also require the operator to take a decision via the operator console (10). The analysis device (7) may also include a module for controlling the (simple or alternated) pulse mode of the transmitter (5) to enable, by means of a step for analyzing the operating state related to the pulses and at least one cleanliness measurement of the ultrasound waves coming out of the second channel, the inspection characteristics of the weld to be extracted for a targeted identification of the anomaly.

In an alternative embodiment of the method, the analysis device (7) corrects the welding parameters by means of the PLC system (9) as a function of the defect detected. It can also inform an operator of these corrections.

The data analyzed during the occurrence of a defect coming from the PLC system (9), the library (8), the interferometer (6) and potentially the operator console (10) are recorded in a database (11) to enable the causes of the defects to be analyzed.

The method according to the invention and the installation enabling the implementation thereof therefore permit a full exploration of the weld and not just the visible surface thereof. This adaptive analysis capacity make it possible to rely progressively less on the vigilance and experience of the operator and to reduce the number of unnecessary re-welds. Very advantageously, they allow the inspection to be carried out with very limited strip-stoppage time, and for the same time as required for the weld if the sliding of at least the wave output of the first channel (52) and the wave input of the second channel (61) is synchronous to the movement of a welding head.

Finally, it is conceivable that the transmitter and/or the receiver and the first and second channels could be electro-acoustic components for generating/capturing the ultrasound waves around the weld structure. However, these components are too large to be coupled within the interstice left by the jaws (of a few centimeters), in particular in the case of thin strips less than a few centimeters thick. This is why the first and second channels are advantageously provided as a small-section optical guide.

The invention claimed is:

1. A method for inspecting a butt weld of two transverse ends of first and second metal strips, the method comprising the following steps:
   bringing together and holding the transverse ends between a first jaw and a second jaw each disposed along a respective one of the transverse ends, leaving at least one space between the first jaw and the second jaw and forming an interstice configured to permit passage of a first transmission channel of incident waves able to generate ultrasound waves on one surface of the first strip and to enable passage of a second transmission channel of waves emerging from a surface of the second strip;
   generating the incident waves of the first channel using laser pulses in an operating state at least configured to implement a third channel of ultrasound waves generated on the surface of the first strip, passing through the weld, and emerging in the second channel; and
   extracting weld inspection characteristics for identification in a step of analyzing the operating state related to the pulses and at least one measurement of a signature of a vibration state of the surface of the second strip upon emergence of the ultrasound waves in the second channel, enabling an inspection of external and internal defects related to a strip-weld-strip structure.

2. The method according to claim 1, which further comprises:
   sending the pulses with a transmitter coupled to an input of the first channel and capturing the waves of the second channel with a receiver coupled to an output of the second channel; and
   sliding an output of the first channel and an input of the second channel along the space between the two jaws without touching the strips, to extract the weld inspection characteristics in two ways:
      synchronously and during a time period as short as possible in relation to a welding device carried by a mechanism slid along the space between the two jaws;
      after completion of welding of the ends of each strip.

3. The method according to claim 1, which further comprises deducing the inspection characteristics of the weld from a measurement of attenuation, traveling time or wave transformation coming from the second channel.

4. The method according to claim 1, which further comprises comparing a signature of a weld being inspected to typical measurement signatures of weld defects catalogued in a database.

5. The method according to claim 1, which further comprises generating alarms as a function of the weld inspection characteristics or signatures extracted.

6. The method according to claim 1, which further comprises implementing the method in one of the following modes:
   a learning mode systematically involving an expert to confirm or modify an identification and quantification of a welding defect;
   an automatic mode in which the analysis step related to the inspection characteristics of the weld independently identifies and quantifies at least one welding defect and issues at least one alarm to an operator subject to a predefined tolerance;
   a semi-automatic mode in which, as part of the preceding automatic mode, if ultrasound wave transfer characteristics are liable to be inadequately identifiable, an additional inspection decision request is sent to an operator.

7. The method according to claim 1, which further comprises implementing the method in one of the following modes:
   a learning mode systematically involving an expert who, on a basis of an identification and quantification of a welding defect, corrects appropriate welding parameters, such as a movement speed of a welding head or a welding power in order to correct the defect;
   an automatic mode in which the analysis step related to the weld inspection characteristics independently corrects welding parameters based on identification and quantification of a welding defect;
   a semi-automatic mode in which, as part of a preceding automatic mode, the analysis step issues a welding-parameter correction request to an operator on a basis of identification and quantification of the welding defect.

8. The method according to claim 1, which further comprises, with a view to analysis steps after an inspection step, recording any identified and quantified faults in a database, jointly and for each defective weld, with welding parameters and data concerning the welded strips.

9. The method according to claim 1, which further comprises generating the ultrasound waves on a surface of the first strip with a pulse laser operating in at least one of the following two states:
a thermoelastic operating state;
a thermoelastic operating state alternating with an ablation operating state, the alternation being determined by the analysis step, in the event of an anomaly, with a possibility of carrying out an additional analysis of characteristics related to a wave transfer.

10. The method according to claim 1, which further comprises causing an ultrasound signal captured by the second channel to undergo a synthetic aperture focusing technique process before the analysis step.

11. A nondestructive weld-testing installation for implementing the method according to claim 1, the installation comprising:
at least one optical guide disposed in at least one of the first or second channels for ultrasound waves.

12. The installation according to claim 11, wherein said at least one optical guide includes one or more optical fibers or a collimator/focalizer moving contactlessly above the surface of the strip ends, in parallel with a welding path.

13. The installation according to claim 11, which further comprises:
a receiver being sensitive to ultrasound waves and coupled to the second channel;
the second channel including at least one optical guide having a wave collecting end moving contactlessly in the interstice between the jaws, along a path parallel and synchronous to a path of the ultrasound waves on the surface of the first strip.

14. The installation according to claim 13, wherein said receiver is an interferometer.

15. The installation according to claim 11, wherein an output of the first channel and an input of the second channel are configured to move contactlessly above the surface of the strip ends and to be synchronized with or delayed in relation to a welding operation along one predefined length of the ends.

16. The installation according to claim 11, which further comprises a pulsed YAG laser generating the pulses being guided through the first channel and generating the ultrasound waves at an output of the first channel on the side of the first strip.

17. The installation according to claim 11, which further comprises a confocal Fabry-Perot or photo-induced electromotive force interferometer ultrasound wave receiver coupled to an output of the second channel.

* * * * *